(12) United States Patent
Lohri

(10) Patent No.: US 8,071,803 B2
(45) Date of Patent: Dec. 6, 2011

(54) PROCESS

(75) Inventor: Bruno Lohri, Reinach BL (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 384 days.

(21) Appl. No.: 12/483,590

(22) Filed: Jun. 12, 2009

(65) Prior Publication Data

US 2009/0312569 A1    Dec. 17, 2009

(30) Foreign Application Priority Data

Jun. 17, 2008  (EP) .................................... 08158432

(51) Int. Cl.
*C07C 69/75* (2006.01)

(52) U.S. Cl. ......................................................... 560/1

(58) Field of Classification Search ........................ None
See application file for complete search history.

(56) References Cited

U.S. PATENT DOCUMENTS

| | | |
|---|---|---|
| 2,899,458 A | 8/1959 | Wilson |
| 4,129,595 A | 12/1978 | Suzuki |
| 2003/0092708 A1 | 5/2003 | Shinkai et al. |
| 2007/0100154 A1 | 5/2007 | Hoffmann et al. |
| 2008/0154059 A1 | 6/2008 | Hoffmann et al. |

FOREIGN PATENT DOCUMENTS

| | | |
|---|---|---|
| EP | 1 020 439 | 7/2000 |
| WO | WO 98/54124 | 12/1998 |
| WO | WO 01/96273 | 12/2001 |
| WO | WO 2004/056752 A1 | 7/2004 |
| WO | WO 2005/003116 | 1/2005 |
| WO | WO 2007/051714 | 5/2007 |

OTHER PUBLICATIONS

Tilford, C. *Jour. of the Amer. Chem. Soc.*, 71 (1949) 1705-1709.
*Database WPI Week 200215*, 2002-114497 XP002507526.
March, Jerry *McGraw-Hill International Book Comp.* Hamburg p. 422, paras 0-97 and p. 426, parsa 0-98.
Shinkai et al., J. Med. Chem., 43, pp. 3566-3572 (2000).
Hauser, M., Journal of the American Chemical Society, vol. 105, pp. 5688-5690 (1983) XP002416563.
March, J. Advanced Organic Chemistry Third Ed. (1985) pp. 388-389, XP002488845.
Roth, et al., J. Med. Chem., vol. 35, No. 9, pp. 1609-1617 (1992) XP002437815.
Creger, P.L., J. Am. Chem. Soc., vol. 92, No. 5, pp. 1397-1398 (1970) XP002437816.
Creger, P.L., Ann. Rep. Med. Chem., 12, pp. 278-287 (1977).
Petragnani et al., Synthesis, pp. 521-578 (1982).
Shiner et al., J. Am. Chem. Soc., 103, pp. 436-442 (1981).
Williams et al., J. Org. Chem., 45, pp. 5082-5088 (1980).
Severin et al., Synthesis, 4, pp. 305-307 (1982).
Tavares et al., J. Med. Chem., 47, pp. 5049-5056 (2004).
Goossen et al., Adv. Synth. Catal., 345, pp. 943-947 (2003).

*Primary Examiner* — Paul A Zucker

(74) *Attorney, Agent, or Firm* — George W. Johnston; Patricia S. Rocha-Tramaloni; Gene J. Yao

(57) ABSTRACT

The present invention relates to a process for the preparation of 1-(2-ethyl-butyl)-cyclohexanecarboxylic acid which is useful as an intermediate in the preparation of pharmaceutically active compounds.

16 Claims, No Drawings

PROCESS

PRIORITY TO RELATED APPLICATION(S)

This application claims the benefit of European Patent Application No. 08158432.8, filed Jun. 17, 2008, which is hereby incorporated by reference in its entirety.

SUMMARY OF THE INVENTION

The present invention relates to a process for the preparation of 1-(2-ethyl-butyl)-cyclohexanecarboxylic acid which is useful as an intermediate in the preparation of pharmaceutical active compounds.

DETAILED DESCRIPTION OF THE INVENTION

In a first aspect, the present invention provides a process for the preparation of a 1-(2-ethyl-butyl)-cyclohexanecarboxylic acid ester derivative of formula (I'):

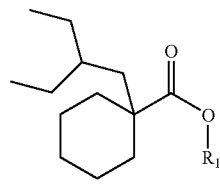
(I')

which comprises reacting a cyclohexanecarboxylic acid ester derivative of formula (II):

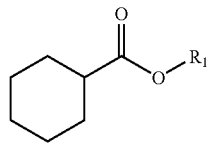
(II)

wherein $R^1$ is a $(C_1-C_8)$alkyl or $(C_3-C_8)$cycloalkyl, with an alkylating agent in the presence of a lithium secondary amide.

In certain particular embodiments $R^1$ is a $(C_5-C_8)$cycloalkyl or a $(C_1-C_6)$alkyl; and more preferably $R^1$ is ethyl, propyl, isopropyl or t-butyl, and most preferably ethyl, propyl or isopropyl. In certain particular embodiments the alkylating agent is a 1-halo-2-ethylbutane or a sulfonate ester of 2-ethyl-1-butanol.

The lithium secondary amide is either available from commercial sources, or is formed by contacting a secondary amine as defined below, with a lithium agent such as a $(C_1-C_6)$alkyllithium, $(C_3-C_6)$cycloalkyllithium or phenyllithium. Preferably, the lithium secondary amide is lithium dicyclohexylamide.

The alkylation may be followed by the cleavage of the ester by using well known methods to obtain 1-(2-ethyl-butyl)-cyclohexanecarboxylic acid, identified as formula (I) below:

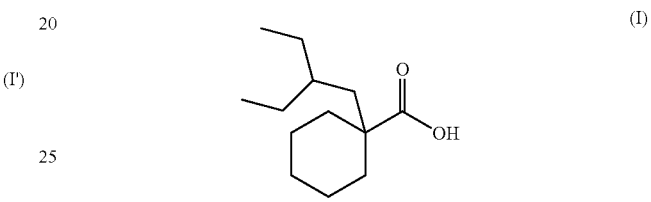
(I)

The compound of formula (II) is generally available from commercial sources or is readily prepared using methods well known to the person skilled in the art (see for instance L. Goossen, A. Döhring, Adv. Synth. Catal. 2003, 345, 943 and references cited therein). For example, a solution of cyclohexanecarboxylic acid in excess alcohol of formula $R^1OH$ is heated after addition of toluenesulfonic acid to obtain a compound of formula (II). One can also add an alkyl halide $R^1X$ to a solution of an alkali metal salt of cyclohexanecarboxylic acid in a solvent such as alcohols (e.g. methanol or ethanol), ether-like solvent (e.g. THF), acetonitrile, DMF and/or water.

The compound of formula (I) may be used as an intermediate in the synthesis of valuable pharmaceutical compounds, such as the ones described in EP 1,020,439.

Accordingly, in another embodiment the present invention provides a process comprising the synthetic steps represented in the following scheme:

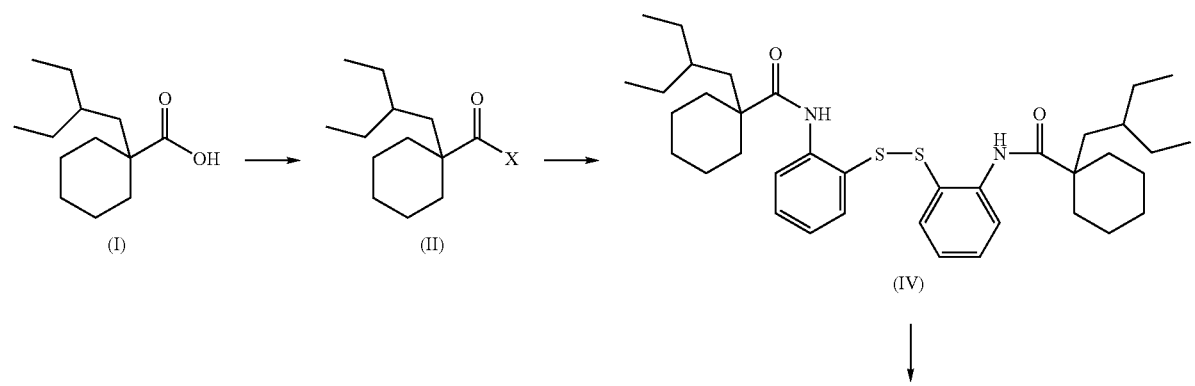

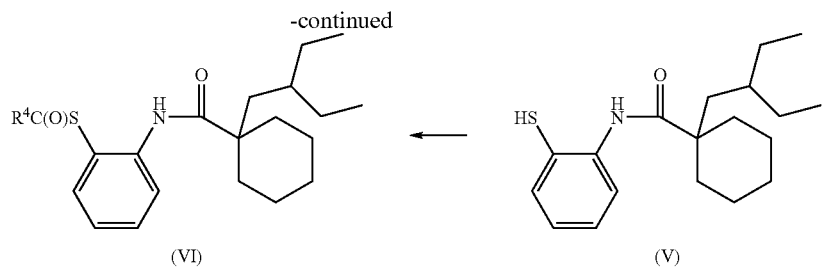

wherein X is I, Br, Cl or F and $R^4$ is a $C_1$-$C_8$ alkyl. In particular, the process comprises reacting 1-(2-ethyl-butyl)-cyclohexanecarboxylic acid (I) with a halogenating agent, such as $PX_3$, $PX_5$, $SOX_2$ or a cyanuric halide, to obtain the acyl halide of formula (III). The halogenating step is preferably carried out in the presence of a tri-($C_1$-$C_5$)alkylamine. Furthermore, the process comprises reacting the acyl halide with bis(2-aminophenyl)disulfide to acylate the amino groups of the (2-aminophenyl)disulfide, reducing the amino-acylated disulfide product with a reducing agent such as triphenylphosphine, zinc or sodium borohydride to yield the thiol product, and acylating the thiol group in the thiol product with $R^4C(O)X'$, wherein X' is I, Br, Cl or F.

The additional steps may be performed, e.g., according to the procedures described in Shinkai et al., J. Med. Chem. 43:3566-3572 (2000) and WO 2007/051714.

Preferably the halogenating agent is chosen from thionyl chloride, phosphorus pentachloride, phosphorus tribromide and cyanuric fluoride, most preferably thionyl chloride. The acyl halide of formula (III) wherein X is Cl is most preferred.

In the thiol acylation step, preferably the acylating agent is $R^4C(O)X'$, wherein X' is Cl. Most preferably $R^4$ is isopropyl.

Unless otherwise stated, the following terms used in the specification and claims have the meanings given below:

The term "halo" means chloro, bromo, iodo or fluoro.

The term "halide" means chloride, bromide, iodide or fluoride.

The term "($C_1$-$C_8$)alkyl" refers to a branched or straight hydrocarbon chain, such as methyl, ethyl, n-propyl, isopropyl, n-butyl, isobutyl, sec-butyl and t-butyl, pentyl, hexyl, heptyl or octyl.

The term "($C_3$-$C_8$)cycloalkyl" refers to a single saturated carbocyclic ring, such as cyclopropyl, cyclobutyl, cyclopentyl, cyclohexyl, cycloheptyl and cyclooctyl.

The term "($C_1$-$C_6$)alkyllithium" is understood as being a ($C_1$-$C_6$)alkyl chain as defined above substituted by a lithium atom, such as butyllithium, hexyllithium, or sec-butyllithium.

The term "substituted phenyl" refers to a phenyl substituted by one or more substituents independently chosen from the group consisting of ($C_1$-$C_3$)alkyl, nitro and a halogen atom such as fluoro, bromo, or chloro.

The term "secondary amine" refers to an amine of formula (a):

(a)

where $R^2$ and $R^3$ may be the same or different and are independently selected from a ($C_1$-$C_6$)alkyl or a ($C_3$-$C_7$)cycloalkyl, or $R^2$ and $R^3$ taken together with the nitrogen atom to which they are attached, form a ($C_4$-$C_8$)heterocycloalkane optionally containing an additional heteroatom of O or N. Representative examples include, but are not limited to, piperidine, 4-methyl-piperidine, piperazine, pyrrolidine, morpholine, dimethylamine, diethylamine, diisopropylamine, dicyclohexylamine, ethylmethylamine, ethylpropylamine and methylpropylamine. Preferably, the secondary amine is diethylamine, diisopropylamine, dicyclohexylamine, ethylmethylamine, ethylpropylamine, methylpropylamine or morpholine, and more preferably diethylamine or dicyclohexylamine. The most preferred secondary amine is dicyclohexylamine.

The term "($C_4$-$C_8$)heterocycloalkane" refers to a saturated non-aromatic cyclic compound of 4 to 8 ring atoms in which one or two ring atoms are heteroatoms of N or O, wherein the ($C_4$-$C_8$)heterocycloalkane is optionally substituted with one or more ($C_1$-$C_3$)alkyl groups (preferably one ($C_1$-$C_3$)alkyl group).

The term "protic acid" refers to a Brönsted acid that donates at least one proton (H+) to another compound. Typical protic acids include mineral acids such as nitric acid, sulfuric acid, phosphoric acid, hydrogen halide acids, strong organic acids such as methanesulfonic acid, benzenesulfonic acid and the like and complex acids such as tetrafluoro boronic acid, hexafluoro phosphoric acid, hexafluoro antimonic acid and hexafluoro arsenic acid. Preferred protic acids are sulfuric acid and hydrobromic acid.

The term "sulfonate ester of 2-ethyl-1-butanol" refers to a substituted or an unsubstituted phenyl-sulfonate, an unsubstituted naphthalene-sulfonate or a ($C_1$-$C_6$)alkylsulfonate ester derivative of 2-ethyl-1-butanol wherein substituted phenyl and the ($C_1$-$C_6$)alkyl chain are as previously defined. Representative examples include, but are not limited to, benzenesulfonic acid 2-ethyl-butyl ester, 1-naphthalenesulfonic acid 2-ethyl-butyl ester, 2-naphthalenesulfonic acid 2-ethyl-butyl ester, toluene-4-sulfonic acid 2-ethyl-butyl ester, 4-nitro-benzenesulfonic acid 2-ethyl-butyl ester, 2,4,6-trimethylbenzenesulfonic acid 2-ethyl-butyl ester, ethanesulfonic acid 2-ethyl-butyl ester, methanesulfonic acid 2-ethyl-butyl ester and butanesulfonic acid 2-ethyl-butyl ester.

In another embodiment, the present invention is directed to a process for the preparation of 1-(2-ethyl-butyl)cyclohexanecarboxylic acid, identified below as formula (I):

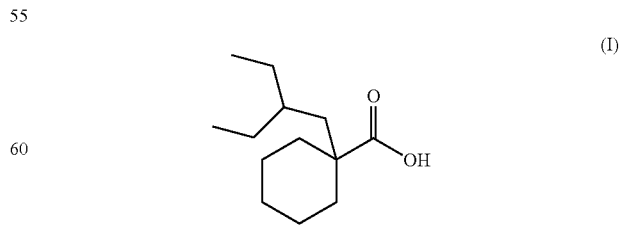

(I)

which comprises an acidic cleavage, wherein a protic acid cleaves a 1-(2-ethyl-butyl)cyclohexanecarboxylic acid ester derivative of formula (I'):

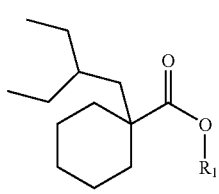

(I')

wherein R¹ is as defined above.

In a further embodiment, the present invention is directed to a process for the preparation of 1-(2-ethyl-butyl)cyclohexanecarboxylic acid, identified below as formula (I):

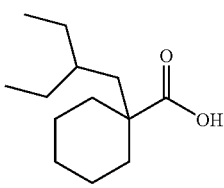

(I)

which comprises an acidic cleavage, wherein sodium iodide promotes the cleavage of a 1-(2-ethyl-butyl)cyclohexanecarboxylic acid ester derivative of formula (I'):

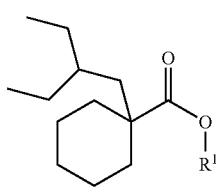

(I')

in the presence of a protic acid, wherein R¹ is as defined above.

In another embodiment, the present invention is directed to a process for the preparation of 1-(2-ethyl-butyl)cyclohexanecarboxylic acid, identified below as formula (I):

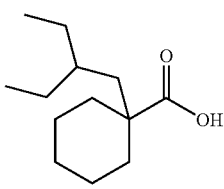

(I)

which comprises the following steps:
a) esterification of cyclohexanecarboxylic acid to obtain a cyclohexanecarboxylic acid ester derivative of formula (II):

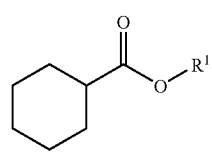

(II)

wherein R¹ is as defined above;

b) reacting said cyclohexanecarboxylic acid ester with an alkylating agent, in the presence of a lithium secondary amide to obtain the compound (I') as defined above;
c) cleaving the ester of compound (I') as defined above to obtain a compound of formula (I).

Preferably the cleavage of the ester (step c) is carried out in the presence of sodium iodide and a protic acid.

The present invention takes place in the presence of an organic solvent such as an ether like solvent (e.g. tetrahydrofuran, diisopropyl ether, t-butylmethyl ether or dibutyl ether), an alcohol solvent (e.g. methanol or ethanol), an aliphatic hydrocarbon solvent (e.g. hexane, heptane or pentane), a saturated alicyclic hydrocarbon solvent (e.g. cyclohexane or cyclopentane) or aromatic solvent (e.g. toluene or t-butyl-benzene).

A nonprotic organic solvent is the preferred solvent during the alkylation, such as tetrahydrofuran, alone or in combination with another nonprotic solvent, e.g. from the group of the apolar solvents hexane, heptane and t-butyl-benzene. Most preferably the nonprotic solvent is tetrahydrofuran.

For the acidic cleavage of the ester (step c, in the presence of protic acid), carboxylic acid (e.g. acetic acid, propionic acid or butyric acid) is the preferred solvent.

The preferred lithium agent is a $(C_1-C_6)$alkyllithium, and butyllithium is the most preferred.

For the preparation of the lithium secondary amide, 0.8 to 1.0 equivalents of butyllithium with respect to secondary amine of formula (a) are preferably used. More preferably, 0.85 to 0.95 equivalents are used. Most preferably 0.9 equivalents are used.

The preferred alkylating agent is 1-halo-2-ethylbutane, most preferably 1-bromo-2-ethylbutane.

The preferred sulfonate ester of 2-ethyl-1-butanol is toluene-4-sulfonic acid 2 ethyl-butyl ester.

Preferably 1.1-1.6 equivalents of 1-bromo-2-ethylbutane are used, more preferably 1.2-1.4 equivalents are used.

The alkylation is performed preferably under an inert gas atmosphere, preferably under argon or nitrogen. In the presence of lithium dicyclohexylamide, the alkylation is preferably carried out at a temperature between −10 and 10° C., most preferably at 0° C.

In a further embodiment, the present invention provides a process for the preparation of S-[2-([[1-(2-ethylbutyl)-cyclohexyl]-carbonyl]amino)phenyl]2-methylpropanethioate comprising the formation of a compound of formula (I) obtained by any of the processes and conditions mentioned previously.

In yet another embodiment of the present invention, an intermediate having formula (I') is provided,

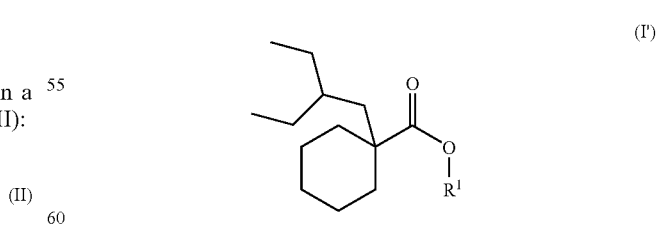

(I')

wherein R¹ is a $(C_1-C_8)$alkyl or a $(C_3-C_8)$cycloalkyl, preferably R¹ is a $(C_1-C_6)$alkyl.

More preferably, R¹ is ethyl, propyl, isopropyl or t-butyl with respect to the intermediate of formula I'. Most preferably, R¹ is ethyl, propyl or isopropyl with respect to the intermediate of formula I'.

The starting materials and reagents, which do not have their synthetic route explicitly disclosed herein, are generally available from commercial sources or are readily prepared using methods well known to the person skilled in the art.

The following examples are provided for the purpose of further illustration and are not intended to limit the scope of the claimed invention.

The following abbreviations and definitions are used: AcOH (Acetic Acid); aq. (aqueous); n-BuLi (n-butyllithium); CDCl$_3$ (deuterated chloroform); d (doublet); DCM (dichloromethane); DEA (diethylamine); eq. (equivalent); g (gram); GC (gas chromatography); h (hour); HBr (hydrobromic acid); HCl (hydrochloric acid); KOH (potassium hydroxide); KOtBu (Potassium tert-butoxide); M (Molar); m (multiplet); Me (methyl); MeOH (methanol); mL (milliliter); N (normality); NaCl (sodium chloride); NaHCO$_3$ (sodium bicarbonate); NaOH (sodium hydroxide); NMR (nuclear magnetic resonance); RT (room temperature); s (singlet); sat. (saturated); t (triplet); TBAB (tetrabutylammonium bromide); TBME (t-butyl methyl ether); THF (tetrahydrofuran); and p-TsOH (p-toluenesulfonic acid monohydrate);

Example 1.1

Preparation of Cyclohexanecarboxylic Acid Ethyl Ester

To a solution of cyclohexanecarboxylic acid (23.1 g, 180 mmol) in ethanol (100 mL) was added p-TsOH (1.027 g, 5.4 mmol). The mixture was heated to 78-79° C., and for several hours solvent was slowly distilled off whereas the volume was kept relatively constant by addition of fresh ethanol. Stirring at reflux temperature was continued overnight. An additional portion of p-TsOH (685 mg, 3.6 mmol) was added and the reaction mixture was stirred at 79° C. for an additional 5 h. The cooled reaction mixture was concentrated to nearly ¼ volume, diluted with TBME and extracted with cold aq. NaHCO$_3$. The aqueous phase was extracted with TBME. The organic phases were washed with water until neutral, combined, dried over sodium sulfate and concentrated to give 26.5 g crude product which was distilled at 40° C. (0.25 mbar) to afford 24.5 g (87%) cyclohexanecarboxylic acid ethyl ester, GC purity >99% (area). $^1$H-NMR (CDCl$_3$, 300 MHz): ppm 1.22 (t, 3H), 1.08-1.80 (m, 8H), 1.85-1.92 (m, 2H), 2.23-2.32 (m, 1H), 4.11 (q, 2H).

Example 1.2

Preparation of Cyclohexanecarboxylic Acid n-Propyl Ester

To cyclohexanecarboxylic acid sodium salt (5.0 g, 33.3 mmol) in THF (80 mL) tetrabutylammonium bromide (1.074 g, 3.33 mmol) and 1-bromopropane (4.545 g, 49.95 mmol) in THF (120 mL) were added. The mixture was stirred 72 h at 50° C., cooled to room temperature and filtered. The precipitate was washed with THF. The filtrate was concentrated and the residue diluted with TBME. The solution was washed with water and the aqueous phases were re-extracted with TBME. The organic phases were combined, dried over sodium sulfate and evaporated to afford 4.2 g (74%) cyclohexanecarboxylic acid n-propyl ester as a liquid, GC purity 99% (area). $^1$H-NMR (CDCl$_3$, 400 MHz): ppm 0.94 (t, 3H), 1.15-1.36 (m, 3H), 1.38-1.50 (m, 2H), 1.55-1.81 (m, 5H), 1.85-1.92 (m, 2H), 2.23-2.32 (m, 1H), 4.02 (q, 2H).

Example 1.3

Preparation of Cyclohexanecarboxylic Acid Isopropyl Ester

To a solution of cyclohexanecarboxylic acid (22.0 g, 172 mmol) in isopropanol (66 mL) and cyclohexane (44 mL) p-TsOH (653 mg, 3.43 mmol) was added. The mixture was heated with stirring to 70-73° C. and solvent was slowly distilled off whereas the volume was kept relatively constant by addition of fresh solvent mixture. After 6 h, a second portion of p-TsOH (653 mg, 3.43 mmol) was added and the reaction mixture was stirred at 71° C. overnight (without distilling off solvent). After a total of 24 h, the cooled reaction mixture was concentrated to ¼ volume. Ice and saturated aq. NaHCO$_3$ were added and the mixture was extracted twice with TBME. The organic phases were washed to neutral with diluted aq. NaCl solution, combined, dried over sodium sulfate and concentrated. The crude product (28.5 g) was distilled at 40° C. (0.2-0.16 mbar) to afford 27.75 g (93%) cyclohexanecarboxylic acid isopropyl ester as a colorless liquid, GC purity 98% (area). $^1$H-NMR (CDCl$_3$, 400 MHz): ppm 1.21 (d, 6H), 1.17-1.34 (m, 3H), 1.35-1.49 (m, 2H), 1.55-1.80 (m, 3H), 1.82-1.92 (m, 2H), 2.20-2.29 (m, 1H), 4.94-5.04 (m, 1H).

Example 1.4

Preparation of Cyclohexanecarboxylic Acid Tert-Butyl Ester

To a solution of cyclohexanecarboxylic acid (10.0 g, 78 mmol) in DCM (75 mL) concentrated sulfuric acid (765 mg, 7.8 mmol) was added. At a temperature between −15° C. and −10° C. isobutylene (10.94 g, 195 mmol) was introduced over 1 h. The cooling bath was removed and the reaction mixture was stirred at room temperature for 72 h. Then a second portion of isobutylene (10.94 g, 195 mmol) was introduced over 1 h at −10° C. The reaction mixture was stirred at room temperature for an additional 20 h, then NaHCO$_3$ (7.864 g, 93.6 mmol) was added before the mixture was stirred at room temperature for another 1 h. Water (50 mL) was added under stirring. After 45 min the reaction mixture was worked up and washed until neutral. The organic phases were combined, dried over sodium sulfate and concentrated on a rotary evaporator. The crude product (13.5 g) was distilled over a Vigreux column at 35° C. (0.04 mbar) to afford 10.9 g (76%) cyclohexanecarboxylic acid tert-butyl ester as a colorless oil. $^1$H-NMR (CDCl$_3$, 400 MHz): ppm 1.12-1.54 (m, 14H), 1.55-1.99 (m, 5H), 2.12-2.22 (m, 1H).

Example 2.1

Preparation of 1-(2-Ethyl-Butyl)-Cyclohexanecarboxylic Acid Isopropyl Ester

To a solution of dicyclohexylamine (14.24 g, 78.5 mmol) in THF (35 mL) 1.6 M n-BuLi in hexane (44.2 mL, 70.7 mmol) was added with stirring over 50 min at temperature between −20° C. and −15° C. The resulting orange suspension was stirred 10 min at −20° C. and then added via a teflon tube over 20 min to a stirred solution of cyclohexanecarboxylic acid isopropyl ester (10.0 g, 58.75 mmol) in THF (75 mL) at 0-2° C. To the resulting solution 1-bromo-2-ethylbutane (13.58 g, 82.25 mmol) in THF (37.5 mL) was added at 0° C. over 15 min. The solution was stirred overnight at 0° C. and for another 3 h at room temperature. At 5° C. ice-water (25 mL) was added, followed by 2N HCl (60 mL). The white suspension was filtered and the filter cake was washed with water and ethyl acetate. The organic phase of the filtrate was washed with sat. aq. NaHCO$_3$ and with aq. NaCl. The aqueous phases were extracted with ethyl acetate. The organic phases were combined, dried over sodium sulfate and concentrated. The crude product (15.5 g) was distilled at 60° C. (0.05 mbar) to give 12.7 g (85%) 1-(2-ethyl-butyl)-cyclohexanecarboxylic acid isopropyl ester as colorless oil, purity 99.2% (GC area).

$^1$H-NMR (CDCl$_3$, 400 MHz): ppm 0.80 (t, 6H), 1.15-1.39 (m, 11H), 1.23 (d, 6H), 1.40 (d, 2H), 1.51-1.59 (m, 2H), 2.02-2.12 (m, 2H). 4.95-5.05 (m, 1H).

Example 2.2

Preparation of
1-(2-Ethyl-Butyl)-Cyclohexanecarboxylic Acid
Isopropyl Ester

To a solution of dicyclohexylamine (4.263 g, 23.5 mmol) in THF (10 mL) 1.6 M n-BuLi in hexane (13.23 mL, 21.15 mmol) was added with stirring over 20 min at temperature between −20° C. and −15° C. This orange suspension was stirred 10 min at −20° C. and then warmed up to 0° C. To this orange suspension a solution of cyclohexanecarboxylic acid isopropyl ester (3.0 g, 17.63 mmol) in THF (22 mL) was added over 15 min at 0° C. The resulting solution was stirred 30 min at 0° C., then 1-bromo-2-ethylbutane (4.073 g, 24.7 mmol) in THF (11 mL) was added at the same temperature over 15 min. Stirring at 0° C. was continued overnight and for an additional 2 h at room temperature. At 5° C. cold water (20 mL) was added, followed by 2N HCl (50 mL). The white suspension was filtered and the filter cake was washed with water and ethyl acetate. The organic phase of the filtrate was washed with sat. aq. NaHCO$_3$ and with aq. NaCl. The aqueous phases were extracted with ethyl acetate. The organic phases were combined, dried over sodium sulfate and concentrated. The crude product (4.7 g) was distilled at 50° C. (0.01 mbar) to give 3.95 g (88%) 1-(2-ethyl-butyl)-cyclohexanecarboxylic acid isopropyl ester as colorless oil, purity 97% (GC area).

Example 2.3

Preparation of
1-(2-Ethyl-Butyl)-Cyclohexanecarboxylic Acid
Isopropyl Ester

To a solution of dicyclohexylamine (2.85 g, 15.7 mmol) in THF (7 mL) 1.6 M n-BuLi in hexane (8.8 mL, 14.1 mmol) was added with stirring over 20 min at −65° C. The suspension was warmed up to −40° C. and then added via a teflon tube over 20 min to a stirred solution of cyclohexanecarboxylic acid isopropyl ester (2.0 g, 11.75 mmol) in THF (15 mL) at −65° C. The resulting solution was stirred 1 h at −65° C., then 1-bromo-2-ethylbutane (2.715 g, 16.45 mmol) in THF (7.5 mL) was added at −65° C. over 15 min. The solution was stirred 1.5 h at −65° C. and then overnight without a cooling bath while slowly warming up to room temperature. At 5° C. ice-water (15 mL) was added, followed by 2N HCl (30 mL). The white suspension was filtered and the filter cake was washed with water and ethyl acetate. The organic phase of the filtrate was washed with sat. aq. NaHCO$_3$ and with aq. NaCl. The aqueous phases were extracted with ethyl acetate. The organic phases were combined, dried over sodium sulfate and concentrated. The crude product (2.9 g) was distilled at 50° C. (0.01 mbar) to give 2.5 g (84%) 1-(2-ethyl-butyl)-cyclohexanecarboxylic acid isopropyl as a colorless oil, purity 93% (GC area) (cyclohexanecarboxylic acid dicyclohexylamide as impurity: not detectable both in distilled and in crude product).

Example 2.4

Preparation of
1-(2-Ethyl-Butyl)-Cyclohexanecarboxylic Acid
Isopropyl Ester

To a solution of diisopropylamine (1.90 g, 18.75 mmol) in THF (9 mL) 1.6 M n-BuLi in hexane (10.6 mL, 16.9 mmol) was added with stirring over 20 min at −65° C. The suspension was warmed up to −40° C. and then added via a teflon tube over 20 min to a stirred solution of cyclohexanecarboxylic acid isopropyl ester (2.393 g, 14.1 mmol) in THF (20 mL) at −65° C. The resulting solution was stirred 0.5 h at −65° C., then 1-bromo-2-ethylbutane (3.249 g, 19.68 mmol) in THF (10 mL) was added at −65° C. over 15 min. The solution was stirred 1.5 h at −65° C. and then overnight without a cooling bath while slowly warming up to room temperature. At 5° C. ice-water (15 mL) was added, followed by 2N HCl (30 mL). The organic phase was diluted with ethyl acetate and washed with sat. aq. NaHCO$_3$ and with aq. NaCl. The aqueous phases were extracted with ethyl acetate. The organic phases were combined, dried over sodium sulfate and concentrated. The crude product (3.5 g) was distilled at 55° C. (0.01 mbar) to give 2.9 g (81%) 1-(2-ethyl-butyl)-cyclohexanecarboxylic acid isopropyl ester as a colorless oil, purity 93% (GC area) (cyclohexanecarboxylic acid diisopropylamide as impurity: 0.9% in dist. product and 0.7% in crude product).

Example 2.5

Preparation of
1-(2-Ethyl-Butyl)-Cyclohexanecarboxylic Acid
Ethyl Ester

To a solution of diisopropylamine (2.37 g, 23.4 mmol) in THF (12 mL) 1.6 M n-BuLi in hexane (13.2 mL, 21.09 mmol) was added with stirring over 20 min at −65° C. The suspension was warmed up to −40° C. and then added via a teflon tube over 20 min to a stirred solution of cyclohexanecarboxylic acid ethyl ester (2.196 g, 14.1 mmol) in THF (20 mL) at −65° C. The resulting solution was stirred 1 h at −65° C., then 1-bromo-2-ethylbutane (3.714 g, 22.5 mmol) in THF (10 mL) was added at −65° C. over 20 min. The solution was stirred 1.5 h at −65° C. and then overnight without a cooling bath while slowly warming up to room temperature. At 5° C. ice-water (15 mL) was added, followed by 2N HCl (30 mL). The organic phase was diluted with ethyl acetate and washed with sat. aq. NaHCO$_3$ and with aq. NaCl. The aqueous phases were extracted with ethyl acetate. The organic phases were combined, dried over sodium sulfate and concentrated. The crude product (3.4 g) was distilled at 50° C. (0.01 mbar) to give 2.6 g (77%) 1-(2-ethyl-butyl)-cyclohexanecarboxylic acid ethyl ester as a colorless oil, purity 92.6% (GC area) (cyclohexanecarboxylic acid diisopropylamide as impurity: 3.8% in dist. product and 3.1% in crude product)

$^1$H-NMR (CDCl$_3$, 400 MHz): ppm 0.80 (t, 6H), 1.12-1.39 (m, 11H), 1.24 (t, 3H), 1.42 (d, 2H), 1.51-1.62 (m, 2H), 2.02-2.12 (m, 2H), 4.11 (q, 2H).

Example 2.6

Preparation of
1-(2-Ethyl-Butyl)-Cyclohexanecarboxylic Acid
Ethyl Ester

To a solution of dicyclohexylamine (15.55 g, 85.77 mmol) in THF (90 mL) 1.6 M n-BuLi in hexane (48.0 mL, 76.8 mmol) was added with stirring over 50 min at temperature between −20° C. and −15° C. The orange suspension was stirred 10 min at −20° C. and then warmed up to 0° C. To this suspension a solution of cyclohexanecarboxylic acid ethyl ester (10.0 g, 64.0 mmol) in THF (30 mL) was added over 15 min at 0° C. The resulting solution was stirred 30 min at 0° C. then 1-bromo-2-ethylbutane (14.79 g, 89.6 mmol) in THF (37.5 mL) was added at the same temperature over 15 min. Stirring was continued 5 h at 0° C. and overnight at room temperature. At 5° C. cold water (25 mL) was added, followed by 2N HCl (60 mL). The white suspension was filtered and the filter cake was washed with water and ethyl acetate. The organic phase of the filtrate was washed with sat. aq. NaHCO$_3$ and with aq. NaCl. The aqueous phases were extracted with ethyl acetate. The organic phases were combined, dried over sodium sulfate and concentrated. The crude product (16.0 g) was distilled at 60° C. (0.05 mbar) to give 12.1 g (79%) 1-(2-ethyl-butyl)-cyclohexanecarboxylic acid ethyl ester as colorless oil, purity 97% (GC area) (cyclohexanecarboxylic acid dicyclohexylamide as impurity: not detectable in distilled product and 0.7% in crude product).

Example 2.7

Preparation of
1-(2-Ethyl-Butyl)-Cyclohexanecarboxylic Acid
Methyl Ester

To a solution of diisopropylamine (2.37 g, 23.4 mmol) in THF (12 mL) 1.6 M n-BuLi in hexane (13.2 mL, 21.09 mmol) was added with stirring over 20 min at −65° C. The suspension was warmed up to −40° C. and then added via a teflon tube over 15 min to a stirred solution of cyclohexanecarboxylic acid methyl ester (2.0 g, 14.1 mmol) in THF (20 mL) at −65° C. The resulting yellow solution was stirred 10 min at −65° C., then it was added over 30 min to a solution of 1-bromo-2-ethylbutane (3.714 g, 22.5 mmol) in THF (10 mL) at 0° C. The solution was stirred 1 h at 0° C. and then overnight without a cooling bath while warming up to room temperature. At 5° C. ice-water (15 mL) was added, followed by 2N HCl (30 mL). The organic phase was diluted with ethyl acetate and washed with sat. aq. NaHCO$_3$ and with aq. NaCl. The aqueous phases were extracted with ethyl acetate. The organic phases were combined, dried over sodium sulfate and concentrated. The crude product (3.3 g) was distilled at 45° C. (0.01 mbar) to give 2.1 g (66%) 1-(2-ethyl-butyl)-cyclohexanecarboxylic acid methyl ester as a colorless oil, purity 92.5% (GC area). The structure of the title compound was confirmed by GC-MS (M=226).

Example 2.8

Preparation of
1-(2-Ethyl-Butyl)-Cyclohexanecarboxylic Acid
n-Propyl Ester

To a solution of dicyclohexylamine (4.281 g, 23.6 mmol) in THF (27 mL) 1.6 M n-BuLi in hexane (13.22 mL, 21.14 mmol) was added with stirring over 50 min at temperature between −20° C. and −15° C. The orange suspension was stirred 10 min at −20° C. and then warmed up to 0° C. To this suspension a solution of cyclohexanecarboxylic acid n-propyl ester (3.0 g, 17.62 mmol) in THF (9 mL) was added over 15 min at 0° C. The resulting solution was stirred 30 min at 0° C., then 1-bromo-2-ethylbutane (4.072 g, 24.67 mmol) in THF (11.25 mL) was added at the same temperature over 15 min. Stirring was continued 5 h at 0° C. and overnight at room temperature. At 5° C. cold water (25 mL) was added, followed by 2N HCl (60 mL). The white suspension was filtered and the filter cake was washed with water and ethyl acetate. The organic phase of the filtrate was washed with sat. aq. NaHCO$_3$ and with aq. NaCl. The aqueous phases were extracted with ethyl acetate. The organic phases were combined, dried over sodium sulfate and concentrated. The crude product (5.1 g) was distilled at 60° C. (0.05 mbar) to give 3.47 g (77%) 1-(2-ethyl-butyl)-cyclohexanecarboxylic acid n-propyl ester as a colorless oil, purity 97% (GC area). $^1$H-NMR (CDCl$_3$, 400 MHz): ppm 0.79 (t, 6H), 0.96 (t, 3H), 1.15-1.42 (m, 10H), 1.41-1.43 (m, 2H), 1.52-1.61 (m, 3H), 1.63-1.70 (m, 2H), 2.06-2.14 (m, 2H), 4.0 (t, 2H).

Example 2.9

Preparation of
1-(2-Ethyl-Butyl)-Cyclohexanecarboxylic Acid
t-Butyl Ester

To a solution of dicyclohexylamine (13.19 g, 72.72 mmol) in THF (90 mL) 1.6 M n-BuLi in hexane (40.7 mL, 65.12 mmol) was added with stirring over 50 min at temperature between −20° C. and −15° C. The orange suspension was stirred 10 min at −20° C. and then warmed up to 0° C. To this suspension a solution of cyclohexanecarboxylic acid t-butyl ester (10.0 g, 54.3 mmol) in THF (30 mL) was added over 15 min at 0° C. The resulting solution was stirred 30 min at 0° C., then 1-bromo-2-ethylbutane (12.54 g, 76.0 mmol) in THF (37.5 mL) was added at the same temperature over 15 min. Stirring was continued 5 h at 0° C. and overnight at room temperature. At 5° C. cold water (25 mL) was added, followed by 2N HCl (60 mL). The white suspension was filtered and the filter cake was washed with water and toluene. The organic phase of the filtrate was washed with sat. aq. NaHCO$_3$ and with aq. NaCl. The aqueous phases were extracted with toluene. The organic phases were combined, dried over sodium sulfate and concentrated. The crude product (12.9 g) was distilled at 60° C. (0.05 mbar) to give 7.6 g (52%) 1-(2-ethyl-butyl)-cyclohexanecarboxylic acid t-butyl ester as a colorless oil, purity 96% (GC area). $^1$H-NMR (CDCl$_3$, 400 MHz): ppm 0.81 (t, 6H), 1.12-1.60 (m, 15H), 1.48 (s, 9H), 1.95-2.05 (m, 2H).

Example 3.1

Preparation of
1-(2-Ethyl-Butyl)-Cyclohexanecarboxylic Acid from
Isopropyl Ester A mixture of 1-(2-Ethyl-butyl)-cyclohexanecarboxylic acid isopropyl ester (10 g, 39.4 mmol) and sodium iodide (886 mg, 5.91 mmol) in AcOH (80 mL) was stirred 50 min at room temperature and then heated to 100° C. 48% aq. HBr (30 mL, 265 mmol) was added dropwise over 30 min. and the reaction mixture was stirred 28 h at 100° C. The cooled reaction mixture was diluted with DCM (120 mL) and ice-water (120 mL). The organic phase was separated and washed with diluted aq. NaCl. The aqueous phases were extracted with another portion of DCM. The organic phases were combined, dried over sodium sulfate and concentrated. The residue (9.1 g) was taken up in 4N NaOH and ice (30 g). The alkaline solution (pH 12) was extracted with DCM (2×50 mL) and made acidic to pH 1 using aq. H$_2$SO$_4$. Extraction with DCM (3×100 mL), washing with diluted aq. NaCl, drying over sodium sulfate and evaporation afforded 7.84 g (94%) 1-(2-ethyl-butyl)-cyclohexanecarboxylic acid, purity 99.3% (GC area, after derivatization with diazomethane). $^1$H-NMR (CDCl$_3$, 300 MHz): ppm 0.81 (t, 6H), 1.15-1.65 (m, 15H), 2.05-2.15 (m, 2H), 12 (broad s, 1H).

Example 3.2

Preparation of
1-(2-Ethyl-Butyl)-Cyclohexanecarboxylic Acid from
Isopropyl Ester 1-(2-Ethyl-butyl)-cyclohexanecarboxylic acid isopropyl ester (3.0 g, 11.8 mmol) was dissolved in ethylene glycol (48 mL). Powdered KOH (6.0 g, 107 mmol) was added and the mixture was stirred 42 h at 160° C. The cooled reaction mixture was slowly added to a stirred mixture of ice-water (120 mL) and 4M $H_2SO_4$ (40 mL), and extracted with DCM (2×120 mL). The organic phases were washed with diluted aq. NaCl until neutral, combined, dried over sodium sulfate and concentrated. The residue (2.5 g) was taken up in 4N NaOH and ice (30 g). The alkaline solution (pH 12) was extracted with TBME (40 mL). The TBME phase was washed twice with 4N NaOH/ice. The basic aqueous phases were made acidic to pH 1 using aq. $H_2SO_4$. Extraction with DCM (2×50 mL), washing with diluted aq. NaCl, drying over sodium sulfate and evaporation afforded 1.5 g (60%) 1-(2-ethyl-butyl)-cyclohexanecarboxylic acid, purity 94.1% (GC area, after derivatization with diazomethane).

Example 3.3

Preparation of 1-(2-Ethyl-Butyl)-Cyclohexanecarboxylic Acid from Ethyl Ester 1-(2-Ethyl-butyl)-cyclohexanecarboxylic acid ethyl ester (2.0 g, 8.32 mmol) was added dropwise under stirring to a solution of KOtBu (3.735 g, 33.3 mmol) in THF (15 mL) containing a small amount of water (225 mg, 12.5 mmol). The mixture was stirred 20 h at 54° C., cooled to room temperature, slowly poured onto a mixture of ice and 4N $H_2SO_4$ and extracted with DCM (2×150 mL) after adjusting to pH 1. The organic phases were washed with diluted aq. NaCl (100 mL), combined, dried over sodium sulfate and concentrated to afford 1.748 g (99%) 1-(2-ethyl-butyl)-cyclohexanecarboxylic acid, purity 95.2% (GC with internal standard).

Example 3.4

Preparation of 1-(2-Ethyl-Butyl)-Cyclohexanecarboxylic Acid from n-Propyl Ester 1-(2-Ethyl-butyl)-cyclohexanecarboxylic acid n-propyl ester (2.3 g, 9.04 mmol) was added dropwise under stirring to a solution of KOtBu (4.058 g, 36.2 mmol) in THF (17 mL) containing a small amount of water (244 mg, 13.6 mmol). The mixture was stirred 20 h at 54° C., cooled to room temperature, slowly poured onto a mixture of ice and 4N $H_2SO_4$ and extracted with DCM (2×150 mL) after adjusting to pH 1. The organic phases were washed with diluted aq. NaCl (100 mL), combined, dried over sodium sulfate and concentrated to afford 1.901 g (99%) 1-(2-ethyl-butyl)-cyclohexanecarboxylic acid, purity 96% (GC area).

Example 3.5

Preparation of 1-(2-Ethyl-Butyl)-Cyclohexanecarboxylic Acid from t-Butyl Ester

To a stirred solution of 1-(2-Ethyl-butyl)-cyclohexanecarboxylic acid t-butyl ester (2.0 g, 7.45 mmol) in AcOH (6 mL) 4M $H_2SO_4$ (0.6 mL, 2.4 mmol) was added dropwise at 95° C. After 18 h at this temperature, another portion of AcOH (4 mL) and 4M $H_2SO_4$ (0.6 mL, 2.4 mmol) was added and stirring at 95° C. was continued for 4 h. Then the reaction was complete according to GC. The reaction mixture was concentrated and then worked up by extraction to afford 1.4 g (88%) 1-(2-ethyl-butyl)-cyclohexanecarboxylic acid, purity 99% (GC area).

The invention claimed is:

1. A process for the preparation of a 1-(2-ethyl-butyl)-cyclohexanecarboxylic acid ester derivative of formula (I'):

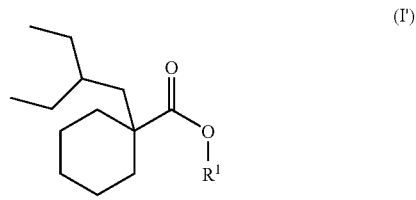

which comprises reacting a cyclohexanecarboxylic acid ester derivative of formula (II):

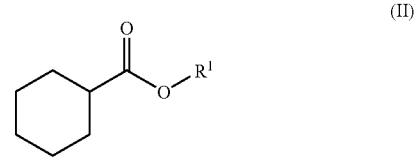

wherein $R^1$ is a $(C_1-C_8)$alkyl or a $(C_3-C_8)$cycloalkyl, with an alkylating agent, in the presence of a lithium secondary amide.

2. A process for the preparation of 1-(2-ethyl-butyl)cyclohexanecarboxylic acid of formula (I):

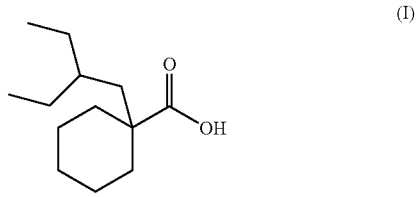

which comprises an acidic cleavage, wherein a protic acid cleaves a 1-(2-ethyl-butyl)cyclohexanecarboxylic acid ester derivative of formula (I'):

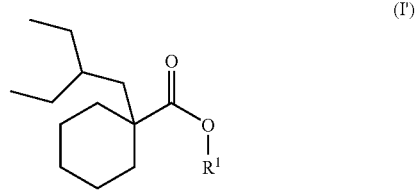

wherein $R^1$ is as defined in claim 1.

3. A process according to claim 2, for the preparation of 1-(2-ethyl-butyl)cyclohexanecarboxylic acid of formula (I), comprising an acidic cleavage wherein sodium iodide promotes the cleavage of a 1-(2-ethyl-butyl)cyclohexanecarboxylic acid ester derivative of formula (I').

4. A process for the preparation of 1-(2-ethyl-butyl)cyclohexanecarboxylic acid of formula (I):

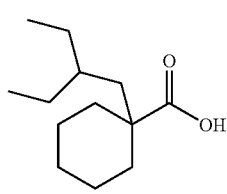
(I)

which comprises the following steps:
a) esterifying cyclohexanecarboxylic acid to obtain a cyclohexanecarboxylic acid ester derivative of formula (II):

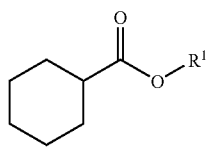
(II)

wherein $R^1$ is a $(C_1\text{-}C_8)$alkyl or a $(C_3\text{-}C_8)$cycloalkyl;
b) reacting said cyclohexanecarboxylic acid ester with an alkylating agent, in the presence of a lithium secondary amide to obtain a compound of formula (I') as defined in claim 1; and
c) hydrolyzing the ester of compound (I') as defined in claim 1 to obtain a compound of formula (I).

5. A process according to claim 1, wherein the lithium secondary amide is formed by contacting a secondary amine, with a lithium agent.

6. A process according to claim 1, wherein the lithium secondary amide is lithium dicyclohexylamide.

7. A process according to claim 4, wherein the cleavage of the ester, step c), is carried out in the presence of sodium iodide and a protic acid.

8. A process according to claim 1, wherein the alkylating agent is 1-bromo-2-ethylbutane.

9. A process according to claim 2, additionally comprising the step of halogenating the compound of formula (I) as defined in claim 2, to obtain a compound of formula (III):

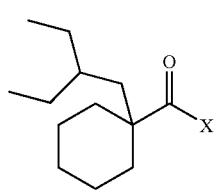
(III)

wherein X is I, Br, Cl or F.

10. The process according to claim 9 additionally comprising the step of acylating a compound of formula IV':

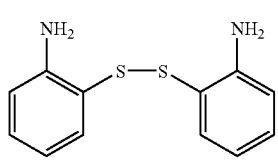
(IV')

with the compound of formula III to obtain a compound of formula IV:

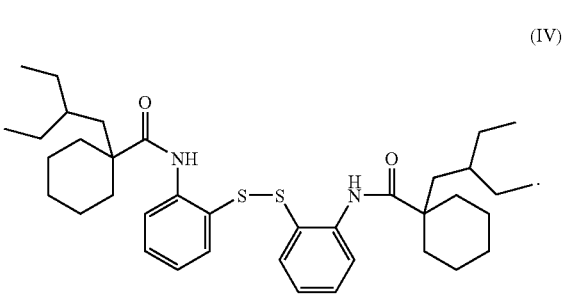
(IV)

11. The process according to claim 10 additionally comprising the step of reducing the compound of formula IV to obtain a compound of formula V:

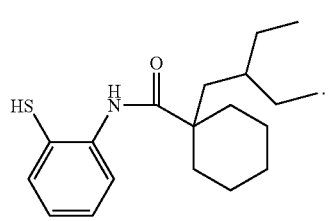
(V)

12. The process according to claim 11 additionally comprising the step of acylating the compound of formula V with $R^4C(O)X'$, wherein X' is I, Br, Cl or F and $R^4$ is a $(C_1\text{-}C_8)$ alkyl, to obtain a compound of formula VI:

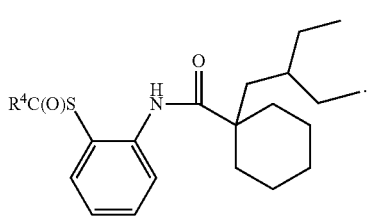
(VI)

13. The process according to claim 1, wherein $R^1$ is ethyl, propyl or isopropyl.

14. A compound of formula (I'):

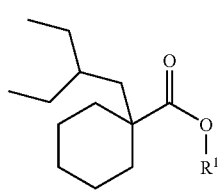
(I')

wherein $R^1$ is a $(C_1\text{-}C_8)$alkyl or $(C_3\text{-}C_8)$cycloalkyl.

15. A compound according to claim 14, wherein $R^1$ is ethyl, propyl, isopropyl or t-butyl.

16. A compound according to claim 14, wherein $R^1$ is ethyl, propyl or isopropyl.

* * * * *